US009173585B2

(12) United States Patent
Tsampazis et al.

(10) Patent No.: US 9,173,585 B2
(45) Date of Patent: Nov. 3, 2015

(54) METHOD AND DEVICE FOR INTRACOCHLEA IMPEDANCE MEASUREMENT

(75) Inventors: Kostas Tsampazis, North Ryde (AU); Paul Carter, West Pennant Hills (AU); Herbert Mauch, Grenzach-Wyhlen (DE)

(73) Assignee: Cochlear Limited, Macquarie University, NSW (AU)

( * ) Notice: Subject to any disclaimer, the term of this patent is extended or adjusted under 35 U.S.C. 154(b) by 1216 days.

(21) Appl. No.: 12/675,969

(22) PCT Filed: Aug. 25, 2008

(86) PCT No.: PCT/AU2008/001253
§ 371 (c)(1),
(2), (4) Date: Dec. 23, 2010

(87) PCT Pub. No.: WO2009/026625
PCT Pub. Date: Mar. 5, 2009

(65) Prior Publication Data
US 2011/0087085 A1    Apr. 14, 2011

(30) Foreign Application Priority Data

Aug. 29, 2007 (AU) .................. 2007904682
Jul. 31, 2008 (AU) .................. 2008903936

(51) Int. Cl.
*A61B 5/053* (2006.01)
*A61N 1/08* (2006.01)
*A61N 1/36* (2006.01)
(Continued)

(52) U.S. Cl.
CPC .............. *A61B 5/053* (2013.01); *A61B 5/6846* (2013.01); *A61N 1/08* (2013.01); *A61N 1/36032* (2013.01); *A61B 5/6817* (2013.01); *A61N 1/0541* (2013.01); *A61N 1/36185* (2013.01)

(58) Field of Classification Search
CPC ............ A61N 1/0541; A61N 1/36032; A61N 1/36185; A61B 5/053; A61B 5/6817
USPC ........... 600/547, 554, 559; 607/55–57, 62–64
See application file for complete search history.

(56) References Cited

U.S. PATENT DOCUMENTS 4,532,930 A   8/1985 Crosby et al.
5,674,264 A   10/1997 Carter et al.
(Continued)

FOREIGN PATENT DOCUMENTS

WO        02/082982 A1   10/2002

OTHER PUBLICATIONS

International Search Report. PCT/AU2008/001253. Mailed Dec. 4, 2008.
(Continued)

*Primary Examiner* — Devin Henson (57) ABSTRACT

This method of determining an intracochlea tissue impedance comprises using at least two stimulating electrodes to apply an electrical stimulus to intracochlea tissue. A voltage caused by the stimulus is measured between two measuring electrodes distinct from the stimulating electrodes. From the voltage a stimulus-response characteristic of tissue between the two measuring electrodes is determined. This allows the tissue/electrode interface impedance and potential and the tissue impedance and potential to be uniquely determined. In turn, modiolus currents can be estimated in monopolar stimulation mode. Also provided is automated initiation of re-mapping of the device when tissue characteristics change.

22 Claims, 5 Drawing Sheets

(51) Int. Cl.
*A61B 5/00* (2006.01)
*A61N 1/05* (2006.01)

(56) References Cited

U.S. PATENT DOCUMENTS

| | | | |
|---|---|---|---|
| 6,751,505 B1 | 6/2004 | Van Den Honert et al. | |
| 7,206,640 B1* | 4/2007 | Overstreet | 607/57 |
| 7,684,856 B2* | 3/2010 | Virtanen et al. | 600/544 |
| 8,014,853 B2* | 9/2011 | Kraus et al. | 600/545 |
| 2005/0101878 A1* | 5/2005 | Daly et al. | 600/559 |

OTHER PUBLICATIONS

Written Opinion. PCT/AU2008/001253. Mailed Dec. 4, 2008.
Micco et al. "Electrical Resistivity Measurements in the Mammalian Cochlea After Neural Degeneration." The Laryngoscope, 2006. vol. 116, pp. 1334-1341.
Vanpoucke, et al. "Identification of the Impedence Model of an Imlanted Cochlear Prosthesis From Intracochlear Potential Measurements." IEEE Transactions on Biomedical Engineering. vol. 51, No. 12, Dec. 2004, pp. 2174-2183.

* cited by examiner

METHOD AND DEVICE FOR INTRACOCHLEA IMPEDANCE MEASUREMENT

CROSS REFERENCE TO RELATED APPLICATIONS

This application is a National Stage of PCT/AU2008/001253, filed Aug. 25, 2008, entitled "METHOD AND DEVICE FOR INTRACOCHLEA IMPEDANCE MEASUREMENT", which claims priority from Australian Provisional Patent Application No. 2007904682, filed Aug. 29, 2007 and Australian Provisional Patent Application No. 2008903936, filed Jul. 31, 2008. The contents of these applications are hereby incorporated by reference herein.

BACKGROUND

1. Field of the Invention

The present invention relates to measurement of electrical characteristics of tissue subjected to electrical stimulation by a cochlear implant.

2. Related Art

Cochlear implant systems bypass the hair cells in the cochlea and directly deliver electrical stimulation to the auditory nerve fibers, thereby allowing the brain to perceive a hearing sensation resembling the natural hearing sensation normally delivered to the auditory nerve. U.S. Pat. No. 4,532,930, the content of which is incorporated herein by reference, provides a description of one type of traditional cochlear implant system.

Cochlear implant systems have typically consisted of an external component referred to as a processor unit and an internal implanted component referred to as a stimulator/receiver unit. These components cooperate to provide the sound sensation to a user.

The external component has a microphone for detecting sounds, such as speech and environmental sounds, a speech processor that converts the detected sounds into a coded signal, a power source such as a battery, and an external transmitter coil.

The coded signal output by the speech processor is transmitted transcutaneously to the implanted stimulator/receiver unit situated within a recess of the temporal bone of the user. This transcutaneous transmission occurs via the external transmitter coil which is positioned to communicate, generally via RF, with an implanted receiver coil provided with the stimulator/receiver unit. This communication serves two purposes, firstly to transcutaneously transmit the coded sound signal and secondly to provide power to the implanted stimulator/receiver unit.

The implanted stimulator/receiver unit includes a receiver coil that receives the coded signal and power from the external processor component, and a stimulator that processes the coded signal and outputs a stimulation signal to an intracochlea electrode assembly or array. The electrode array applies the electrical stimulation directly to the auditory nerve producing a hearing sensation corresponding to the original detected sound.

Following implantation, and at subsequent times as physiological changes occur, there is a need to determine the actual performance of the electrode array and the response of the auditory nerve to stimulation. Data collection for this purpose enables detection and confirmation of the normal operation of the device, and allows stimulation parameters to be optimized to suit the characteristics of the patient. This procedure can include determination of patient specific parameters such as threshold levels (T levels) and maximum comfort levels (C levels) for each stimulation channel. Such data collection can be performed manually in a clinical setting by relying on subjective recipient responses, or by taking measurements directly from the cochlea such as by recording a neural response to stimulation in the manner set out in International Patent Publication No. WO 02/082982, the content of which is incorporated herein by reference. Users' T and C levels vary over time whether permanently such as in the case of tissue degradation, or temporarily for example in the case of the user having a short term disease. For optimal device function it is therefore important to clinically re-fit the device at regular intervals, however this is labor intensive.

Impedance measurements may also be made of the cochlea tissue. Existing impedance measurement techniques used in cochlear implant devices apply a stimulus with an electrode pair, and measure the voltage across that electrode pair. Such an impedance measurement provides information about the total impedance between the two stimulating electrodes, which can be useful to determine the functional condition of the implant. However, the voltage measured arises not only from the tissue impedance between the electrodes, but also from the electrode/tissue interface impedance at each electrode. The electrode/tissue interface impedance depends on the condition and the size of the electrode contact surface area and the amplitude of the stimulation current. The electrode/tissue interface impedance dominates and masks the tissue impedance. It is therefore difficult to precisely determine the tissue impedance and the biological condition of the tissue from such voltage measurements.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

In one aspect of the present invention, a method determining an intracochlea tissue impedance is provided. The method comprises applying an electrical stimulus to intracochlea tissue with at least two stimulating electrodes; measuring a voltage caused by the stimulus between two measuring electrodes distinct from the stimulating electrodes; and determining from the voltage a stimulus-response characteristic of tissue between the two measuring electrodes.

In a second aspect of the present invention, a cochlear implant system for determining an intracochlea tissue impedance is provided. The cochlear implant system comprises an implantable electrode array comprising a plurality of electrodes for applying electrical stimuli to intracochlea tissue; and a controller adapted to cause application of an electrical stimulus to intracochlea tissue by at least two stimulating electrodes, to cause measurement of a voltage caused by the stimulus between two measuring electrodes distinct from the at least two stimulating electrodes, and to determine from the voltage a stimulus-response characteristic of tissue between the two measuring electrodes.

In a third aspect of the present invention, a method of measuring a tissue response arising from a stimulus is provided. The method comprises applying an electrical stimulus to the tissue using at least two stimulating electrodes; after the stimulus, open circuiting the stimulating electrodes and measuring a residual two point potential between the stimulating electrodes; after the stimulus, measuring a residual potential between two non-stimulating electrodes, referred to as a residual four point potential; and comparing the measured two point potential to the measured four point potential to determine at least one of a residual tissue potential and a residual electrode/tissue interface potential.

In a fourth aspect of the present invention, a cochlear implant system for measuring a tissue response arising from a stimulus is provided. The cochlear implant system comprises an implantable electrode array comprising a plurality of electrodes for applying Metrical stimuli to intracochlea tissue; and a controller adapted to apply an electrical stimulus to the tissue using at least at least two stimulating electrodes; after the stimulus, open circuit the stimulating electrodes and measure a residual two point potential between the stimulating electrodes; after the stimulus, measure a residual potential between two nonstimulating electrodes, referred to as a residual four point potential; and compare the measured two point potential to the measured four point potential to determine at least one of a residual tissue potential and a residual electrode/tissue interface potential.

In a fifth aspect of the present invention, a method for estimating modiolus currents induced in a cochlea by electrical stimulation is provided. The method comprises determining an intra-cochlea tissue impedance $Z_{t1}$ between a first intra-cochlear electrode and a second intra-cochlear electrode by a four point impedance measurement; determining an intra-cochlea tissue impedance $Z_{t2}$ between the second intra-cochlear electrode and a third intra-cochlear electrode by a four point impedance measurement; while passing a current between a fourth intra-cochlear electrode and an extra-cochlear electrode, measuring respective voltages $V_1$, $V_2$ and $V_3$ arising at the first, second and third intra-cochlear electrodes; determining respective intra-cochlea tissue currents $I_{t1}$ and $I_{t2}$ flowing through the intracochlea tissue impedances $Z_{t1}$ and $Z_{t2}$ as being $I_{t1}=(V_1-V_2)/Z_{t1}$ and $I_{t2}=(V_2-V_3)/Z_{t2}$; and determining that a modiolus current $I_{m2}$ arising in the proximity of the second electrode due to the current between the fourth intra-cochlear electrode and the extra-cochlear electrode is $I_{m2}=I_{t2}-I_{t1}$.

In a final aspect of the present invention, a method of automated initiation of re-mapping of a cochlear implant is provided. The method comprises obtaining measurements of tissue response to electric stimulation; comparing the tissue response measurements with previously obtained tissue response measurements, to identify any changes which have occurred over time in the tissue response to stimulation; and upon identification of a change in tissue response, initiating re-mapping of the cochlear implant.

BRIEF DESCRIPTION OF THE DRAWINGS

Illustrative embodiments of the present invention will now be are described herein with reference to the accompanying figures, in which.

DETAILED DESCRIPTION

Figure 1A:
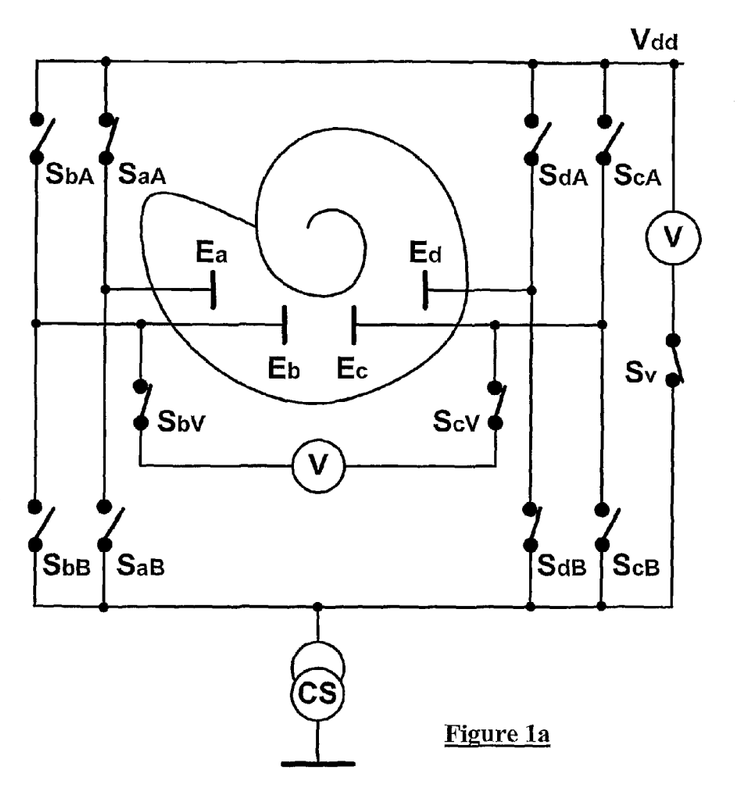
FIGS. 1a and 1b illustrate a system for four point impedance measurement in accordance with one embodiment of the invention.
Figure 1B:
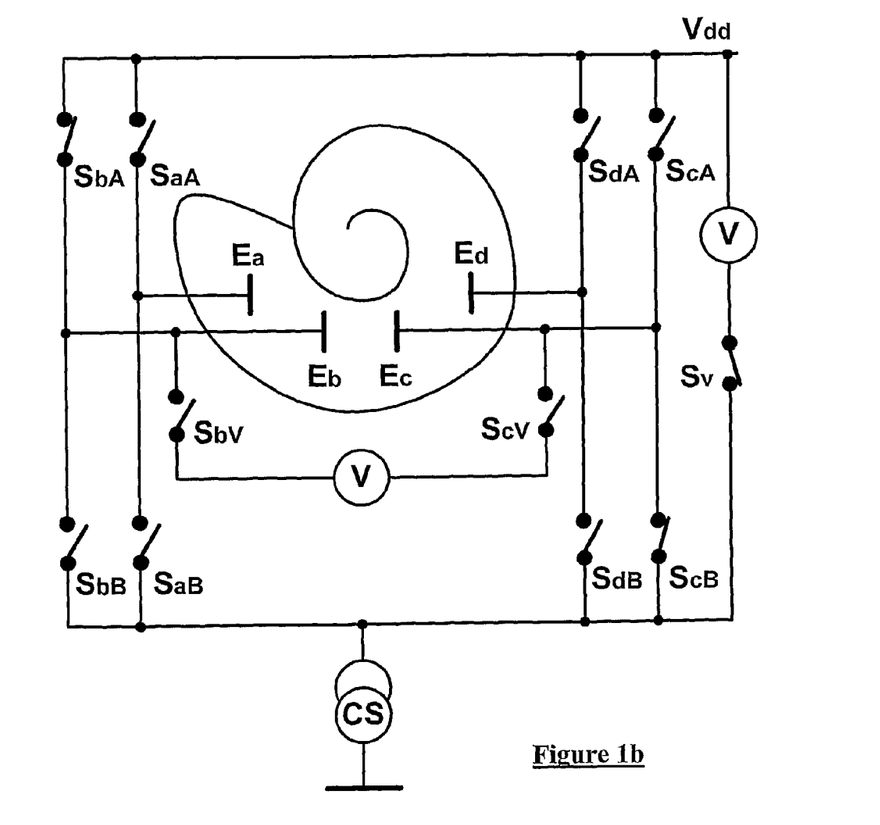

FIGS. 1a and 1b illustrate a system for four point impedance measurement in accordance with one embodiment of the invention. Two electrode pairs are used, selected from the electrodes of a cochlear implant electrode array. As will be discussed in further detail below, in this embodiment the voltage is measured between two measuring electrodes that are not used to apply the stimulus. This type of measurement is referred to herein as a four point measurement.

The current stimulation pair $E_a$ and $E_d$ are used to stimulate the cochlear tissue. The biphasic current path is as follows. During phase 1, a constant stimulation current, set by the programmed current source CS, flows from the power supply rail $V_{dd}$, through the associated switch of the chosen indifferent electrode to the power supply rail $S_{aA}$, the indifferent electrode $E_a$, the intracochlea tissue, the active electrode $E_d$ and its associated switch $S_{dB}$ to the current source. During phase 2, a constant stimulation current with the same amplitude as in phase 1 flows from the power supply rail $V_{dd}$, through switch $S_{dA}$, the indifferent electrode Ed, the intracochlea tissue, the active electrode Ea and its associated switch $S_{aB}$ to the current source CS.

A second electrode pair $E_b$ and $E_c$, being the voltage measurement pair, together with separate switching circuitry, are used to measure the voltage arising from the biphasic stimulation applied by $E_a$ and $E_d$. The voltage difference between electrodes $E_b$ and $E_c$ depends almost solely on the tissue impedance between them, with the stimulation current being constant.

Notably, while the $E_a$ and $E_d$ electrode/tissue interface impedances, and the impedance of the switches $S_{aA}$, $S_{aB}$, $S_{dB}$ and $S_{dA}$ affect the current source output voltage, such impedances do not contribute to the voltage measured between electrodes $E_b$ and $E_c$.

The $E_b$ and $E_c$ electrode/tissue interface impedances and the impedance of the voltage switches $S_{bv}$ and $S_{cv}$ are in series with the input impedance of the associated voltage measurement circuitry. However, as the input impedance of the voltage measurement circuitry is very high and practically no current flows through it, closing switches $S_{bv}$ and $S_{cv}$, places the measuring electrodes $E_b$ and $E_c$ in a high input impedance state during the four point measurement. The measured voltage thus arises almost entirely from the tissue voltage between electrodes $E_b$ and $E_c$, and does not depend on their electrode surface contact impedances and the impedance of the voltage switches $S_{bv}$ and $S_{cv}$.

The polarity of the voltage measured at electrodes $E_b$ and $E_c$ reverses with the change in current direction between phase 1 and phase 2. Accordingly, the input of the associated voltage measurement circuitry is connected in a differential mode. The measured impedance (being the measured voltage difference between electrodes $E_b$ and $E_c$ divided by the stimulation current) is then the tissue impedance between electrodes $E_b$ and $E_c$.

The voltage measurement electrode pair $E_b$ and $E_c$ may be used for two-point impedance measurement, by disconnecting them from the voltage measurement circuitry (switches $S_{bv}$ and $S_{cv}$ "OFF") as shown in FIG. 1b. Such a two-point impedance measurement obtains a measure of the sum of $E_b$ and E0 electrode/tissue interface impedance and the tissue impedance between them. As the tissue impedance between $E_b$ and $E_c$ is already known from the four-point impedance measurement, the remaining impedance can be halved to obtain an estimate of the individual electrode/tissue interface impedance. Thus, the present embodiment makes it possible to identify the contributions to total impedance and also possible to identify mechanisms leading to impedance variations. It is further possible to display the stimulation pulse voltage measured on the current and the voltage electrode pairs.

Thus, the four-point intracochlea impedance measurement described with reference to the system of FIGS. 1a and 1b gives the same cochlear implant functional information such as identifying instances of out of compliance or short/open circuited electrodes, when measuring the voltage over the current stimulating electrodes at the current source. Moreover, the embodiment of FIGS. 1a and 1b also provides information about the tissue impedance when measuring the voltage over the voltage measuring electrodes $E_b$ and $E_c$. The tissue impedance provides information about the biological condition and reaction of the tissue during current stimulation. This is significant information that can be used for intra-cochlea tissue diagnosis and/or study.

Moreover, the measurement method of FIGS. 1a and 1b allows measurement of the tissue impedance at different current levels, and may allow detection of the threshold stimulation level. In turn, automation of the mapping process for customizing the cochlear implant to the particular recipient may be assisted by such information.

By providing for measurement of the voltage between two measuring electrodes which are not used to apply the stimulus, the above discussed embodiment, provides for measurement of a voltage which arises almost entirely from the tissue impedance between the measuring electrodes in response to the stimulus, and/or from the voltage potential distribution within the tissue. In particular, the present embodiment provides for a voltage measurement which is substantially unaffected by any voltage arising from tissue/electrode interface impedance. The measured tissue impedance, determined by comparing the measured voltage to the delivered current, in turn may provide information about the biological condition and reaction of the tissue during and/or after current stimulation. Moreover, embodiments of the invention may in turn provide for determination of the electrode surface-to-tissue impedance, by using the measuring electrodes as stimulating electrodes, referred to herein as a two point measurement.

In some embodiments, a change in tissue response identified over time or identified in response to differing stimuli may be indicative of a threshold at which the respective stimuli caused a neural response. For example, the stimulus may be altered in a stepwise fashion to find a threshold stimulus level (T level) at which neural responses first arise. Similarly, the stimulus may be altered in a stepwise fashion in order to determine a maximum comfort level (C level) at which a sum total of neural responses caused by stimuli along the length of the auditory nerve exceeds a patient comfort level.

An embodiment will now be described that provides automated tissue impedance monitoring and re-mapping. This embodiment provides a way of deducing changes in T and C levels more accurately than before by measuring both the four point impedance at an electrode and its voltage during stimulation on another electrode.

The system of this embodiment periodically measures the four point impedance at an electrode and its voltage during stimulation on another electrode. The measured values are then used to calculate the predicted change in current flowing over the nerve. The T and C levels are then changed in inverse proportion to the change in current flowing over the nerve in order to compensate for the new stimulus conditions. The goal of such automated updating of the device T and C parameters is to prevent the recipient's sound perception from changing for the negative when tissue impedance (current distribution) changes, as the appropriate stimulation current change is performed automatically without requiring clinician re-fitting of the device.

In this embodiment, impedance/potential measurements are taken for all electrode combinations of stimulation pair, and in each instance for all electrode combinations of measurement pair. The current flowing over the auditory nerve at each electrode is then be determined by reference to the modiolus current. The self-monitoring device then identifies which if any stimulation electrodes should be re-mapped. The remapping process can be conducted either by the patient, after a prompt from the system, or automatically. For example, the initiation of re-mapping may simply comprise the device indicating to the user that re-mapping is required, for example by illuminating a LED on the external component of the implant or by playing back a perceivable recorded message via the implanted electrodes and auditory nerve. Once the user has been alerted to the need for remapping, such re-mapping may be carried out manually by the user or a clinician. Alternatively the initiated re-mapping may be conducted by the device, and may comprise the device altering T levels and/or C levels stored by the device by an amount commensurate with the identified change in tissue response, and may even be performed without the user being made aware that re-mapping is being performed.

In an embodiment, the measurements of tissue response are obtained regularly, for example periodically, throughout the lifetime of the device. The measurements of tissue response may comprise tissue impedance measurements, whether obtained from stimulating electrodes in a two point measurement technique or obtained from non-stimulating electrodes in a four point measurement technique such as the method of the first aspect of the present invention. Additionally or alternatively, the measurements of tissue response may comprise residual potential measurements arising from and measured following a tissue stimulus. The residual potential measurements may be obtained by a two point measurement technique, and/or by a four point measurement technique for example in accordance with the method of the third aspect of the invention. The measurements of tissue response may additionally or alternatively comprise estimation of modiolus currents performed in accordance with the method of the fourth aspect of the present invention.

Figure 2:
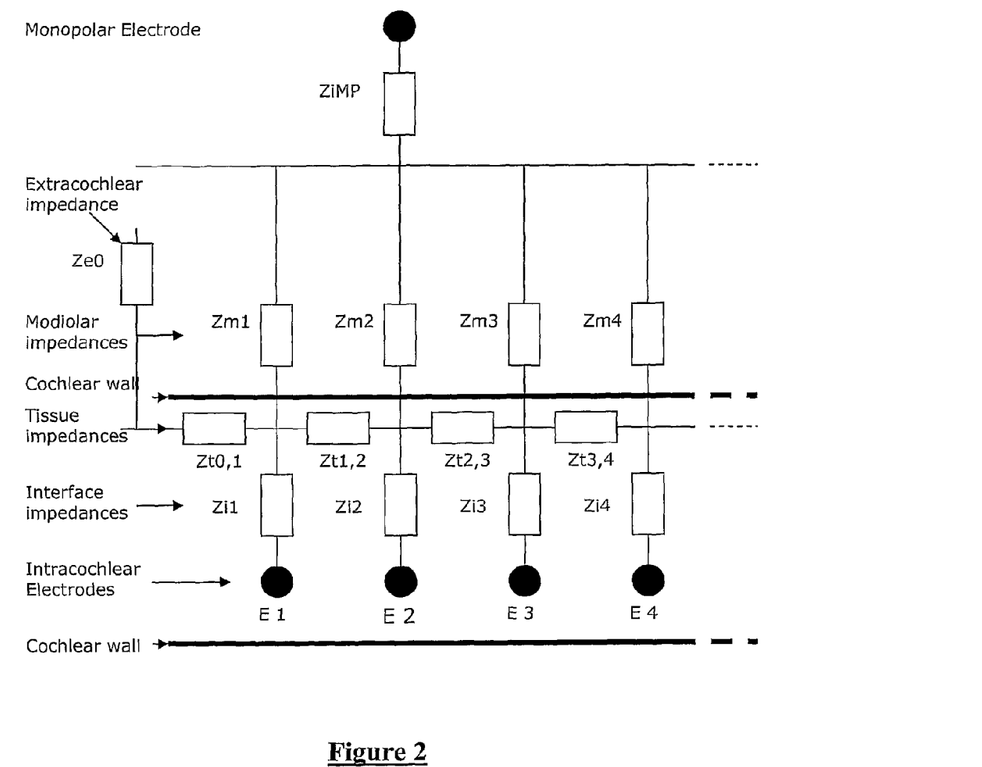
FIG. 2 is an equivalent circuit of the cochlea when subjected to monopolar stimulation.

A diagram showing an equivalent circuit of the cochlea when subjected to monopolar stimulation is shown in FIG. 2. This is used to calculate the currents flowing in the modiolus impedances, $Z_m$, as follows.

First, four point impedance measurements are made for all electrodes along the array. This involves passing current through electrodes n and n+3 and simultaneously measuring the voltage between electrodes n+1 and n+2. This is done for all electrodes on the array (e.g., values of n from 1 to 19 for a 22 electrode array). Given that the cochlea is a perilymph-filled cavity encased in bone, and that perilymph has a low resistivity compared with bone, the impedances within the cochlea, $Z_i$ and $Z_t$, are much smaller than the impedances within the bone, $Z_m$. Therefore it is a reasonable approximation that the four point impedance values obtain in the above manner give the approximate values for the tissue impedances, $Z_t$.

Next, a current is passed between electrode 1 and the monopolar electrode and at the same time the voltages on electrodes 2 to 22 (for a 22 electrode array) are measured. Then current is passed between electrode 2 and the monopolar electrode and the voltage on all electrodes other than electrode 2 is measured. This is repeated on all electrodes to produce a table of voltages. It is possible to take each measurement in a few tens of microseconds in modern cochlear implants so that the whole table can be compiled in a fraction of a second.

Subsequently, from the table of voltages and the four point impedances, the currents flowing in the tissue impedances, $Z_t$, are calculated which in turn gives the currents in the modiolus impedances $Z_m$. These currents are determined by noting that when current is passed between electrode 1 and the monopolar electrode the current flow in tissue impedance $Z_{tn,n+1}$ is simply the voltage difference measured between electrodes n and n+1 divided by the four point impedance, $Z_{tn,n+1}$. That is, $$I_{n,n+1} = (V_n - V_{n+1})/Z_{tn,n+1}$$

where $I_{n,n+1}$ is the current flowing in the tissue impedance $Z_{tn,n+1}$ between electrodes n and n+1, $V_n$ is the voltage measured on electrode n, $V_{n+1}$ is the voltage measured on electrode n+1, and $Z_{tn,n+1}$ is the four point impedance measured between electrodes n and n+1.

Using the model in FIG. 2 it is then possible to derive the current flowing in the modiolus impedances, $Z_{mn}$, because this will be the difference between the current $I_{n-1,n}$ and the current $I_{n,n+1}$. That is, $$I_{mn} = I_{n-1,n} - I_{in,n+1}$$

where $I_{mn}$ is the current flowing into the modiolus impedance $Z_{mn}$ at electrode n, $I_{n-1,n}$, n is the current flowing in the tissue impedance $Z_{tn-1,n}$ between electrodes n−1 and n, and $I_{n,n+1}$ is the current flowing in the tissue impedance $Z_{tn,n+1}$ between electrodes n and n+1.

Figure 3A:
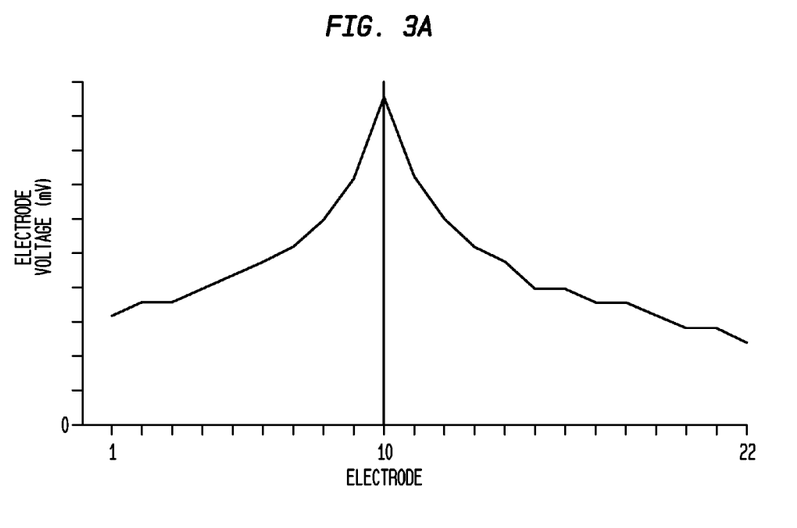
FIGS. 3a and 3b respectively illustrate the voltage and current distributions along an electrode array in response to a monopolar stimulus.

The current flowing in these modiolus impedances $Z_{mn}$ are important as they approximate the current flowing over the nerve and are likely to be closely related to the percept they induce for the user. A sketch of typical voltages measured while current is passed between electrode 10 and the monopolar electrode is show in FIG. 3a, while a sketch showing the corresponding modiolus current is shown in FIG. 3b.

Figure 3B:
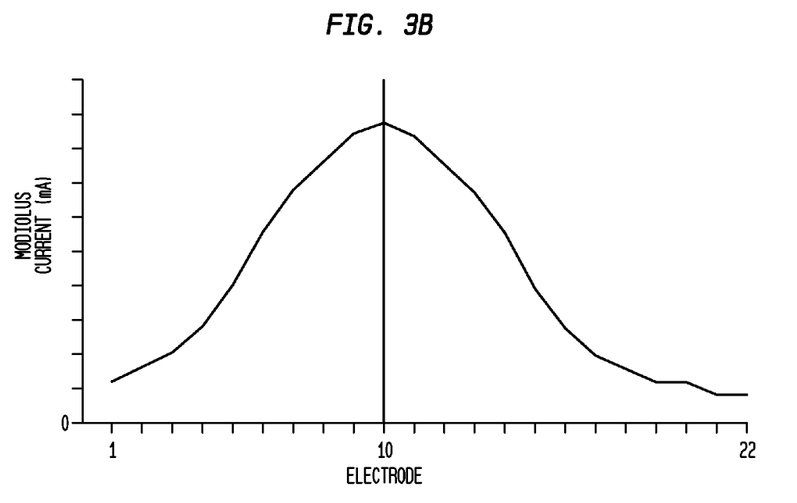

Curves similar to FIG. 3b are also determined for stimulation current applied to each electrode other than electrode 10. A set of 22 curves is therefore obtained representing the current flow into the modiolus (and over the nerve) for monopolar stimulation applied for all 22 electrodes. These curves give a measure of the current flowing across the auditory nerve. In this embodiment, an original set of such curves is obtained at the time the recipient had their T and C levels set, and stored in the device. A new set of curves would then be periodically remeasured automatically.

Such re-measurement may be done without alerting the recipient, by using levels of stimulation current below the hearing threshold for the recipient. As tissue normally behaves linearly with stimulation current, the curves established at a sub-threshold current level can for many purposes be scaled proportionally to any stimulation current.

These remeasured curves can be compared against the originally measured curves. Adjustments to the recipient's T and C levels can then be made as follows. T and C levels are initially set for the recipient as normal. At the same time the set of curves as described above are measured. Once the recipient leaves the clinic the curves are automatically remeasured periodically and the T and C levels are adjusted based on any changes to the curves, in a predefined way. For example, a simple formula to determine the new T level for a single electrode n, based on the recorded impedance for that pair could be as follows:

$$T_{new,n} = T_{original,n} * \frac{I_{m,peak,n,original}}{I_{m,peak,n,new}}$$

where $T_{new,n}$=the new value of T level for electrode n to be used in the recipient's map, $T_{original,n}$=the original value of the recipient's T level for electrode n measured by a clinician, $I_{m,peak,n,new}$=the new peak modiolus current for electrode n (i.e. the highest value of the curve for electrode n) calculated some time after the original T level was set, and $I_{m,peak,n,original}$=the peak modiolus current for electrode n (i.e. the highest value of the curve for electrode n) measured when the original T level was set.

To update C level, it is noted that the C level perceived by the recipient is more likely to be related to the sum of current flow across all electrodes. Therefore in this embodiment the formula used to derive the new C level is:

$$C_{new,n} = C_{original,n} * \frac{\sum_{all\ electrodes} I_{m,original,n}}{\sum_{all\ electrodes} I_{m,new,n}}$$

where $C_{new,n}$=the new value of C level for electrode n to be used in the recipient's map, $C_{original,n}$=the original value of C level for electrode n measured by the clinician, $\Sigma_{all\ electrodes} I_{m,new,n}$—the sum of all $I_m$ values for stimulation on electrode n as measured some time after the original C level was set, and $\Sigma_{all\ electrodes} I_{m,original,n}$=the sum of all $I_m$ values for stimulation on electrode n as measured when the original C level was set.

Figure 4:
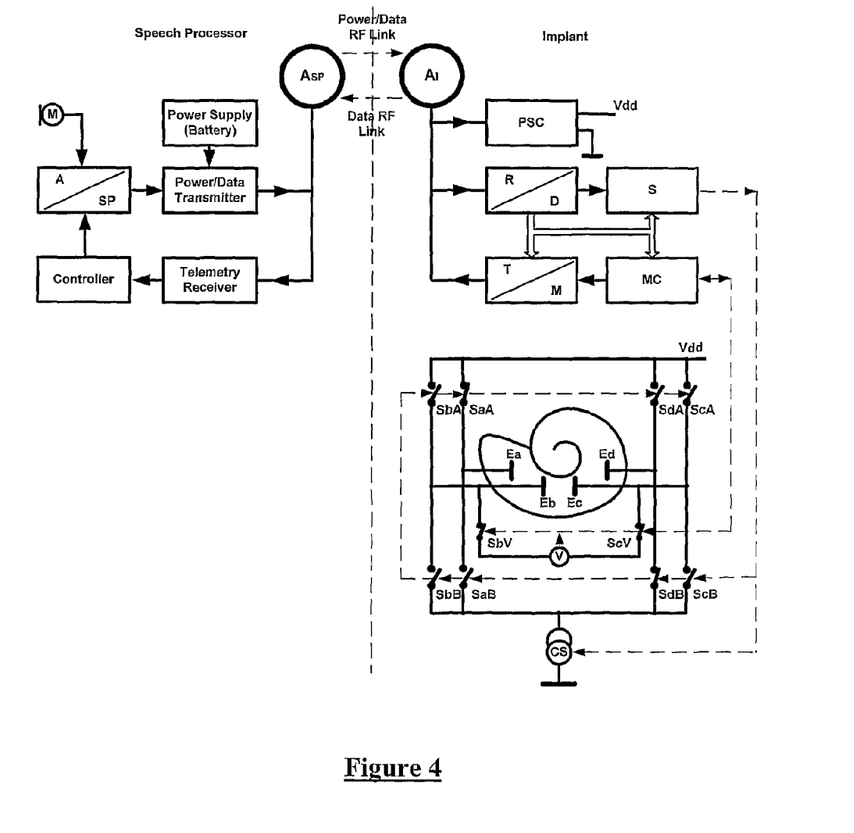
FIG. 4 is a schematic diagram of a cochlear implant system for implementing an embodiment of the present invention.

A schematic diagram of a cochlear implant system comprising an external speech processor and implant operable to apply the proposed mapping process is shown in FIG. 4. The implant's antenna coil AI is connected to the implant's power supply circuitry PSC and the implant's receiver/demodulator circuitry R/D. The R/D drives the implant's stimulation circuitry S. The implant's measurement circuitry MC obtains measurements from the cochlea as described in the preceding, and communicates with the implant's modulator/transmitter circuitry M/T.

The implant's current source CS, power supply rail $V_{dd}$, current stimulation electrodes (stimulation pair) $E_a$ and $E_d$, voltage measurement electrodes (measurement pair) $E_b$ and $E_c$, switches $S_{aA}$ and $S_{aB}$, $S_{dA}$ and $S_{dB}$, $S_{bA}$ and $S_{bB}$, and $S_{cA}$ and $S_{cB}$, differential voltage measurement circuitry V, and switches $S_{bV}$ and $S_{cV}$ are as described previously with respect to FIG. 1.

The external speech processor comprises antenna coil ASP, microphone M, amplifier circuitry A and speech processor circuitry SP.

Figure 5:
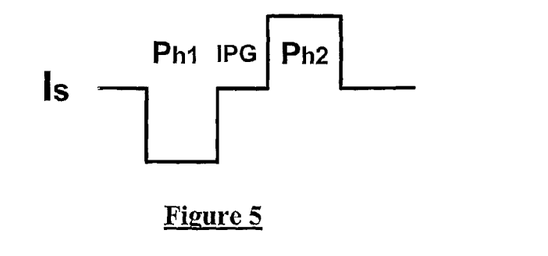
FIG. 5 illustrates the shape of a current pulse used for cochlea neuron stimulation.

FIG. 5 illustrates the shape of the current pulse used for cochlea neuron stimulation. $I_s$ is a current stimulation pulse (pulse amplitude), Ph1 is Phase 1 of the current stimulation pulse (pulse duration), Ph2 is Phase 2 of the current stimulation pulse (pulse duration) and IPG is the interphase gap (interphase gap duration).

The speech processor is inductively coupled with the implant via RF link and provides the implant with power and data for stimulation and measurement. The speech processor also receives data such as measurement results from the implant via the RF link.

Any tissue impedance change and current profile change in $I_m$ can be detected by the four point impedance measurement circuitry and voltage measurement circuitry. Such a change may be indicative of changed T or C levels due to changed stimulation current distribution. The measured values are transmitted to the speech processor from the implant, and can be used for adjustment of the T and/or C level parameters stored by the device. The speech processor will thereafter transmit appropriate stimulus data to the implant which will adjust the amplitude of the stimulation current to compensate for the measured change. Ideally, this compensation minimizes or avoids any change in the patient's perception resulting from the tissue impedance change. The T/C parameters can be adjusted automatically by an appropriate algorithm of the processor, or manually by the patient or a clinician.

The preceding embodiment thus monitors the tissue response for changes which may occur over time, by applying a standard test stimulus to the tissue and identifying changes over time in measurements obtained during such a stimulus.

In a second embodiment, tissue measurements may be obtained in order to obtain a profile of the tissue response with respect to changes in stimulus. In this embodiment, a two point voltage measurement is obtained from the stimulation electrodes during the interphase gap. During the interphase gap two point measurement, the electrodes are floating, disconnected from the stimulation circuitry. This two point measurement obtains a voltage which arises from the double layer potential at each electrode/tissue interface and from the residual hearing neurons/tissue potential (charge) between the stimulation electrodes. Also during the interphase gap, a four point voltage measurement is obtained, being the voltage across a pair of intracochlea measurement electrodes located between the stimulation electrodes. The four point measurement provides information about the residual hearing neurons/tissue charge, with the substantial absence of the double layer potential at each electrode/tissue interface. Together, the two point and four point measures enable the double layer potential and the tissue potential to be separately determined.

In the second embodiment, desired ranges or values of stimulus parameters are determined as follows.

First, a four point measurement of the hearing neurons/tissue impedance is performed during Phase 1 of the stimulation. This is achieved during Phase 1 by switches $S_{aA}$ and $S_{dB}$ being switched "ON" while all other switches to the power supply rail $V_{dd}$ and the current source CS are switched "OFF" (see FIG. 1). The stimulation current flows from the power supply rail $V_{dd}$ through electrode Ea, cochlea neurons/tissue located between electrodes $E_a$ and $E_d$, and electrode $E_d$ to the Current Source (CS). The impedance of the hearing neurons/tissue located between the stimulation electrodes $E_a$ and $E_d$ can be measured (for a particular hearing neurons/tissue segment) by the voltage measurement electrodes $E_b$ and $E_c$ connected to a differential voltage measurement circuitry V through switches $S_{bV}$ and $S_{cV}$.

Second, a four point measurement of the hearing neurons/tissue potential response during the interphase gap is obtained. To obtain this measurement, during the interphase gap all switches to the power supply rail $V_{dd}$ and the current source CS are switched "OFF". The hearing neurons/tissue potential response is measured by electrodes $E_b$ and $E_c$ connected to a differential voltage measurement circuitry V through switches $S_{bV}$ and $S_{cV}$.

Third, a four point measurement of the hearing neurons/tissue impedance is obtained during Phase 2 stimulation. To obtain this measurement, during Phase 2 switches $S_{dA}$ and $S_{aB}$ are switched "ON" while all other switches to the power supply rail $V_{dd}$ and the current source CS are switched "OFF". The stimulation current flows from the power supply rail $V_{dd}$ through electrode $E_d$, cochlea neurons/tissue located between electrodes $E_d$ and $E_a$, electrode $E_a$ to the Current Source (CS). The impedance of the hearing neurons/tissue located between the stimulation electrodes $E_d$ and $E_a$ is measured (for a particular hearing neurons/tissue segment) by the voltage measurement electrodes $E_b$ and $E_c$ connected to differential voltage measurement circuitry V through switches $S_{bV}$ and $S_{cV}$.

Finally, a two point measurement of the electrode polarization potential is obtained during the interphase gap. This is obtained by applying a further biphasic stimulus on electrodes $E_b$ and $E_c$. During Phase 1, switches $S_{bA}$ and $S_{sB}$ are switched "ON" while all other switches to the power supply rail $V_{dd}$ and the current source CS are switched "OFF". The stimulation current flows from the power supply rail $V_{dd}$ through electrode $E_b$, cochlea neurons/tissue located between electrodes $E_b$ and $E_c$, electrode $E_c$ to the Current Source (CS). As a result of the current flow through electrodes $E_b$ and $E_c$, their respective capacitive electrode/tissue interfaces are polarizing. During the interphase gap all switches to the power supply rail $V_{dd}$ and the current source CS are switched "OFF". The polarization potential of electrodes $E_b$ and $E_c$ is then measured by the differential voltage measurement circuitry V connected to the polarized electrodes $E_b$ and $E_c$ through switches $S_{bV}$ and $S_{cV}$. During Phase 2, switches $S_{cA}$ and $S_{bB}$ are switched "ON" while all other switches to the power supply rail $V_{dd}$ and the current source CS are switched "OFF". The charge balancing phase 2 stimulation current flows from the power supply rail $V_d$d through electrode $E_c$, cochlea neurons/tissue located between electrodes $E_c$ and $E_b$, electrode $E_b$ to the Current Source (CS), de-polarizing the tissue interfaces of electrodes $E_b$ and $E_c$. This measurement allows the electrode double layer capacitance formed at the interface electrode/tissue due to stimulation current flow to be calculated.

The four types of measurement described above are conducted for different stimulation pulse frequencies, by varying the duration of the biphasic stimulation pulse, and are also conducted for varying stimulation amplitudes by linearly increasing the stimulation current. Such stimulation parameter variations enable a profile of tissue response with respect to varying stimulation to be obtained. Such profiles can then be obtained for each combination of electrode stimulation pair and electrode measurement pair giving a cochlea impedance distribution map.

The results of such measurements allow real time automated mapping and/or adaptive stimulation to be performed based on the tissue impedance measurement, to optimize the recipient's sound perception.

In the above discussed embodiments, the stimulating electrodes comprise a stimulating electrode pair, however an alternative number of stimulating electrodes may be used. For example, in the embodiment of FIGS. 1a and 1b, the two measuring electrodes are interposed between the stimulating electrode pair, to provide for a measurement configuration in which the measuring electrodes are in a region of large voltage gradient and such that a voltage differential between the measuring electrodes is large. However, in alternative embodiments, the or further measuring electrodes may be positioned to one side of the stimulating electrodes, provided that a measurable voltage differential arises across the measuring electrodes in response to the stimulus. Such laterally positioned measuring electrodes may be particularly useful in providing information regarding the voltage distribution from the stimulated tissue between the stimulating electrodes to the non-stimulated tissue in the vicinity of the laterally positioned measuring electrodes. Such information may assist in investigating the biological condition of the intracochlea tissue.

All documents, patents, journal articles and other materials cited in the present application are hereby incorporated by reference.

It will be appreciated by persons skilled in the art that numerous variations and/or modifications may be made to the invention as shown in the specific embodiments without departing from the spirit or scope of the invention as broadly described. For example, the techniques of the present invention may be applied in conjunction with neural response telemetry. The present embodiments are, therefore, to be considered in all respects as illustrative and not restrictive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The invention claimed is:

1. A method of determining an intracochlea tissue impedance, the method comprising:
    applying an electrical stimulus to intracochlea tissue with at least two stimulating electrodes;
    measuring a voltage caused by the stimulus between two measuring electrodes, wherein the two measuring electrodes are different electrodes than the stimulating electrodes;
    determining, from the measured voltage, the impedance of tissue between the two measuring electrodes;
    comparing the determined impedance of the tissue between the two measuring electrodes with a previously obtained impedance of the tissue between the two measuring electrodes obtained in response to a previously applied stimulus; and
    identifying, based on the comparing, any changes to the impedance of the tissue between the two measuring electrodes.

2. The method of claim 1, further comprising:
    determining an electrode surface-to-tissue impedance of at least one of the measuring electrodes by applying a stimulus using the at least one measuring electrode and measuring a voltage across the measuring electrodes in response to the stimulus applied using the at least one measuring electrode.

3. The method of claim 1, wherein the electrical stimulus is a biphasic stimulus comprising first and second pulses of opposite polarity and an inter-phase gap between the first and second pulses.

4. The method of claim 3, wherein a four point impedance measurement is obtained during at least one of the first pulse and the second pulse.

5. The method of claim 3, wherein a four point potential measurement is obtained during at least one of the interphase gap and a time after the second pulse, to yield a measure of residual voltage.

6. The method of claim 1, further comprising:
    applying the electrical stimulus with characteristics that are substantially the same as characteristics of the previously applied stimulus to enable identification of changes in tissue response over time.

7. The method of claim 1, further comprising:
    applying the electrical stimulus with different characteristics from characteristics of the previously applied stimulus in order to investigate variations in tissue response arising from differing stimuli.

8. The method of claim 1, further comprising:
    placing the measuring electrodes in a high input impedance state during measurement.

9. The method of claim 1, wherein the stimulating electrodes comprise a stimulating electrode pair.

10. The method of claim 9, wherein the measuring electrodes are interposed between the stimulating electrode pair.

11. The method of claim 1, further comprising iteratively repeating the method and altering a characteristic of the electrical stimulus between each iteration, and determining from changes in the impedance of the tissue between the two measuring electrodes a threshold stimulus level (T level) at which neural responses first arise.

12. The method of claim 1, further comprising iteratively repeating the method for a plurality of different measuring electrodes along an auditory nerve, altering a characteristic of the electrical stimulus between each iteration, and determining a maximum comfort level (C level) at which a sum total of neural responses caused by stimuli along the length of the auditory nerve exceeds a patient comfort level.

13. A cochlear implant system for determining an intracochlea tissue impedance, the cochlear implant system comprising:
    an implantable electrode array comprising a plurality of electrodes for applying electrical stimuli to intracochlea tissue; and
    a controller adapted to:
        cause application of an electrical stimulus to intracochlea tissue by at least two stimulating electrodes;
        cause measurement of a voltage caused by the stimulus between two measuring electrodes, wherein the two measuring electrodes are different electrodes than the at least two stimulating electrodes;
        determine, from the measured voltage, the impedance of tissue between the two measuring electrodes;
        compare the determined impedance of the tissue between the two measuring electrodes with a previously obtained impedance of the tissue between the two measuring electrodes obtained in response to a previously applied stimulus; and
        identify, based on the comparing, any changes to the impedance of the tissue between the two measuring electrodes.

14. The cochlear implant system of claim 13, wherein the controller is further adapted to:
    determine an electrode surface-to-tissue impedance of at least one of the measuring electrodes by applying a stimulus using the at least one measuring electrode and measuring a voltage across the measuring electrodes in response to the stimulus applied using the at least one measuring electrode.

15. The cochlear implant system of claim 13, wherein the electrical stimulus is a biphasic stimulus comprising first and second pulses of opposite polarity and an inter-phase gap between the first and second pulses.

16. The cochlear implant system of claim 15, wherein the controller is adapted to cause a four point impedance measurement to be obtained during at least one of the first pulse and the second pulse.

17. The cochlear implant system of claim 15, wherein the controller is adapted to cause a four point potential measurement to be obtained during at least one of the interphase gap and a time after the second pulse, to yield a measure of residual voltage.

18. The cochlear implant system of claim 13, wherein the controller is adapted to:
   cause application of the electrical stimulus with characteristics that are substantially the same as characteristics of the previously applied stimulus to enable identification of changes in tissue response over time.

19. The cochlear implant system of claim 13, wherein the controller is adapted to:
   cause application of the electrical stimulus with different characteristics from characteristics of the previously applied stimulus in order to investigate variations in tissue response arising from differing stimuli.

20. The cochlear implant system of claim 13, wherein the controller is adapted to:
   cause the measuring electrodes to be placed in a high input impedance state during measurement.

21. The cochlear implant system of claim 13, wherein the stimulating electrodes comprise a stimulating electrode pair.

22. The cochlear implant system of claim 21, wherein the measuring electrodes are interposed between the stimulating electrode pair.

* * * * *